US008148393B2

(12) United States Patent
van Dalen et al.

(10) Patent No.: US 8,148,393 B2
(45) Date of Patent: Apr. 3, 2012

(54) ZOLPIDEM TABLETS

(75) Inventors: Frans van Dalen, Nijmegen (NL); Korinde Annemarie Jansen, Loo (NL); Farid Abedin Dorkoosh, Utrecht (NL)

(73) Assignee: Synthon BV, Nijmegen (NL)

(*) Notice: Subject to any disclaimer, the term of this patent is extended or adjusted under 35 U.S.C. 154(b) by 1027 days.

(21) Appl. No.: 11/561,737

(22) Filed: Nov. 20, 2006

(65) Prior Publication Data
US 2007/0166380 A1   Jul. 19, 2007

Related U.S. Application Data

(60) Provisional application No. 60/737,811, filed on Nov. 18, 2005.

(51) Int. Cl.
*A61K 31/44* (2006.01)
*A61K 47/00* (2006.01)
*A61K 9/20* (2006.01)
*A61K 9/22* (2006.01)
*A61K 9/24* (2006.01)

(52) U.S. Cl. ........ 514/300; 514/781; 514/923; 424/464; 424/465; 424/468; 424/471; 424/472

(58) Field of Classification Search .................. 514/300
See application file for complete search history.

(56) References Cited

U.S. PATENT DOCUMENTS

| 2,736,682 A | | 2/1956 | Hermelin |
| 3,048,526 A | | 8/1962 | Boswell |
| 3,388,041 A | | 6/1968 | Gans et al. |
| 3,862,140 A | | 1/1975 | Zinnes et al. |
| 4,382,938 A | | 5/1983 | Kaplan et al. |
| 4,626,538 A | | 12/1986 | Dusza et al. |
| 4,692,337 A | * | 9/1987 | Ukigaya et al. ............... 424/469 |
| 4,794,185 A | | 12/1988 | Rossey et al. |
| 4,824,678 A | | 4/1989 | Lindahl et al. |
| 4,948,592 A | | 8/1990 | Ayer et al. |
| 5,047,246 A | * | 9/1991 | Gallian et al. ................ 424/464 |
| 5,178,867 A | | 1/1993 | Guittard et al. |
| 5,292,461 A | | 3/1994 | Juch et al. |
| 5,681,583 A | | 10/1997 | Conte et al. |
| 5,891,891 A | | 4/1999 | Benincasa |
| 6,126,969 A | | 10/2000 | Shah et al. |
| 6,136,345 A | * | 10/2000 | Grimmett et al. ............. 424/471 |
| 6,242,460 B1 | | 6/2001 | Ettema et al. |
| 6,248,363 B1 | | 6/2001 | Patel et al. |
| 6,281,360 B1 | | 8/2001 | Ettema et al. |
| 6,309,668 B1 | | 10/2001 | Bastin et al. |
| 6,372,255 B1 | | 4/2002 | Saslawski et al. |
| 6,514,531 B1 | * | 2/2003 | Alaux et al. .................. 424/468 |
| 2002/0058066 A1 | * | 5/2002 | Tomohira et al. ............. 424/480 |

FOREIGN PATENT DOCUMENTS

| EP | 0 050 563 | 5/1984 |
| EP | 0 251 859 | 11/1990 |
| GB | 2 245 492 A | 1/1992 |
| WO | WO 00/33835 | 6/2000 |

OTHER PUBLICATIONS

Martine Schmitt et al., "Imidazo [1,2-*b*] pyridazines. XXIII Some 5-Deaza Analogues, Syntheses of Some 2-Aryl-6-(chloro, methoxy or unsubstituted)-3-(variously substituted) imidazo[1,2-α] pyridines and Their Affinity for Central and Mitochondrial Benzodiazepine Receptors", *Aust. J. Chem.*, 1997, 50, pp. 719-725.
Giuseppe Trapani et al., "Synthesis and Binding Affinity of 2-Phenylimidazo [1,2,α] pyridazines Derivatives for both Central and Peripheral Benzodiazepine Receptors. A New Series of High-Affinity and Selective Ligands for the Peripheral Type" *J. Med. Chem.*, 1997, 40, pp. 3109-3118.
P. George et al., "Zolpidem and Related Compounds: Syntheses, Physical Properties and Structure Activity Relationships", *Imidazopyridines in Sleep Disorders*, Raven Press, New York, 1988, pp. 11-23.
W. C. Gunsel et al., "Compression-Coated and Layer Tablets", *Pharmaceutical Dosage Forms: Tablets* vol. 1, Marcel Dekker, Inc., New York, 1989, pp. 247-284.
N. G. Lordi, "Sustained Release Dosage Forms", *The Theory and Practice of Industrial Pharmacy*, Lea & Febiger; 3RD edition (Aug. 1986), Chapter 14, pp. 430-446.
"Types and Classes of Tablets", *The Theory and Practice of Industrial Pharmacy*, Lea & Febiger; 3RD edition (Aug. 1986) pp. 329-333.

* cited by examiner

*Primary Examiner* — Johann Richter
*Assistant Examiner* — Nathan W Schlientz
(74) *Attorney, Agent, or Firm* — Mark R. Buscher

(57) ABSTRACT

A zolpidem tablet having modified release is designed as a tablet-in-tablet dosage form.

14 Claims, No Drawings

ZOLPIDEM TABLETS

This application claims the benefit of priority under 35 U.S.C. §119(e) from U.S. provisional patent application Ser. No. 60/737,811, filed Nov. 18, 2005, the entire contents of which are incorporated herein by reference.

BACKGROUND OF THE INVENTION

1. Field of the Invention

The present invention relates to a tablet containing the hypnotic agent zolpidem, which provides a modified and/or extended release.

2. Description of the Related Arts

Zolpidem (or N,N,6-trimethyl-2-(4-methylphenyl)-imidazo[1,2-s]pyridine-3-acetamide) is a rapid acting hypnotic agent having the following formula.

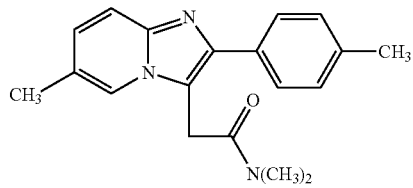

The compound was disclosed generically in EP 50563 of Synthelabo. A tartaric acid addition salt of zolpidem, having a molar ratio of two zolpidem per one acid molecule, frequently referred to in the literature as zolpidem hemitartrate but more correctly denominated as zolpidem tartrate, was disclosed in EP 251859/U.S. Pat. No. 4,794,185. Zolpidem tartrate has been marketed as an immediate release tablet for oral application by human patients under the trade marks AMBIEN® and STILNOX®. In these commercial pharmaceutical dosage forms, zolpidem is present as a salt with L(+)tartaric acid wherein the molar ratio of zolpidem to tartaric acid is 2:1. These zolpidem tablets are conventional film coated tablets for immediate release of the active substance after ingestion and they contain 5 or 10 mg of zolpidem tartrate. The inactive ingredients are: lactose, microcrystalline cellulose, sodium starch glycolate, hydroxypropylmethylcellulose and magnesium stearate. The film coating layer consists of hydroxypropylmethylcellulose, polyethylene glycol and colorants.

While zolpidem is a rapidly acting hypnotic, it is also a rapidly eliminated hypnotic agent. As a result, zolpidem typically starts acting within 15-30 minutes, or less, after ingestion of the tablet and its action can typically last for approximately 4-6 hours. However, this duration of action can be considered too short in some circumstances. Lengthening the duration of action would thus be desirable.

U.S. Pat. No. 6,514,531 suggests formulating zolpidem in a controlled release dosage form that exhibits biphasic release. One of the embodiments which is shown in the examples therein relate to the formation of a bilayer tablet; i.e., a tablet with two parallel layers, one containing zolpidem tartrate within an immediate release formulation, the other containing zolpidem tartrate within a modified release formulation. Recently, a commercial product was launched in the U.S., AMBIEN CR, that is a bilayer tablet made apparently according to U.S. Pat. No. 6,514,531.

However, a bilayer tablet can exhibit certain disadvantages. In particular, both layers are adhered to each other by compression. Thus, they may be separated relatively easily by improper handling. Further, film-coating of both layers is essentially necessary. Moreover, the exemplified bilayer tablets made in the U.S. Pat. No. 6,514,531 use wet granulation, which can be less economical, to form a granulate which is then compressed into the tablet layer.

Another dosage form proposed in U.S. Pat. No. 6,514,531 for providing biphasic release, albeit only in Example 10 thereof and not described in the text, is a compression coated tablet, also known as a "tablet-in-tablet" concept. The dosage form comprises an inner tablet that is covered by an outer coat that is compressed onto the inner tablet. Both inner and outer parts are made by a compression process that is characteristic for making tablets, hence the "tablet-in-tablet" expression. In general for biphasic release the outer coat comprises an immediate release composition and the inner core comprises a modified release composition. U.S. Pat. No. 6,514,531 shows such a zolpidem tablet-in-tablet dosage form.

The main advantage of a tablet-in-tablet formulation compared to the bilayer formulation is that the immediate release layer and the modified release layer are in a fixed position in relation to each other and, once successfully formed, cannot be easily separated during subsequent storage and handling. A film coat protection, which is almost required of the bilayer formulation, is essentially not necessary.

On the other hand, the disadvantage of the tablet-in-tablet concept is the limitation in size, shape and excipients; i.e., not all pharmaceutical compositions are susceptible of being formulated as a tablet-in-tablet. For example, it can be difficult to make a physically stable tablet and/or a tablet having sufficiently high hardness and low friability. In addition, the tabletting process may not be sufficiently robust for large scale production without difficulty.

Indeed, attempts to repeat the teaching of the Example 10 of U.S. Pat. No. 6,514,531 revealed that the produced tablets were not suitable for use in actual pharmaceutical applications as the tablets generally had low hardness, higher friability and exhibited capping or laminating in the tabletting process in relatively high frequency. Therefore, a substantive modification of the disclosed concept is necessary if a tablet-in-tablet dosage form is to be successful.

SUMMARY OF THE INVENTION

The present invention is directed to the discovery of robust zolpidem tablet-in-tablet oral dosage forms. Thus, a first aspect of the invention relates to a zolpidem oral tablet, comprising:

(a) an inner tablet core comprising zolpidem or a pharmaceutically acceptable salt thereof and a controlled release matrix; and (b) a compression coating layer surrounding said inner tablet core, which comprises an effective amount of zolpidem or a pharmaceutically acceptable salt thereof and at least one pharmaceutically acceptable excipient; wherein the tablet meets at least one of the following criteria:

(i) the mass of said coating layer is at least 2.5 times the mass of said tablet core;

(ii) the mass of said coating layer is at least 2 times the mass of said tablet core and said coating layer contains at least 30% of a binder; or (iii) the mass of said coating layer is at least 1.8 times the mass of said tablet core and said coating layer contains at least 34% of a binder.

The present inventors have discovered that the mass and/or size of the inner tablet core should be significantly smaller than the mass of the outer coating/total size of the tablet. Additionally, as the mass ratio of the core to the coating becomes smaller, the need for a significant amount of binder in the coating becomes more apparent. By satisfying one of the three criteria, a pharmaceutically elegant tablet-in-tablet dosage form can be made for delivering zolpidem. In particular, the preferred range of the core:coat mass ratio is 1:3 to 1:5 w/w. The overall tablet is generally about 11 millimeters in diameter or less and the inner tablet core is typically about 7 millimeters in diameter or less. Advantageously, both the inner tablet core and the outer coat layer are made by direct compression of a homogenized mixture of their respective components.

DETAILED DESCRIPTION OF THE INVENTION

The present invention relates to modified release pharmaceutical compositions containing zolpidem. For simplicity reasons, and in absence of the indications to the contrary, the word "zolpidem" within the whole description means zolpidem per se as well as its pharmaceutically acceptable salts. In this regard all of the zolpidem salts disclosed or mentioned in U.S. Pat. No. 6,242,460 are contemplated as being useful in compositions of the present invention. Specific examples of zolpidem salts include zolpidem hydrochloride, zolpidem hydrochloride monohydrate, zolpidem hydrochloride ethanolate, zolpidem methane sulfonate, zolpidem tosylate, zolpidem maleate, zolpidem hydrobromide, zolpidem fumarate, zolpidem sulfate, zolpidem tartrate and zolpidem hydrogen tartrate. The preferred salt of zolpidem is zolpidem tartrate; i.e., a 2:1 ratio of zolpidem to tartaric acid.

The composition of the present invention is in the form of a tablet-in-tablet wherein the inner core tablet is a controlled release composition and the surrounding outer compression coating layer applied thereover is an immediate release composition. The outer coating layer serves to provide an immediately effective amount of zolpidem; e.g. sufficient to induce sleep, while the controlled release core provides for an elongation of the period of action. In this way, effective blood plasma levels of zolpidem are extended for a longer period of time, thereby extending the sleep/hypnotic effects.

The tablet core comprises zolpidem and a controlled release matrix. The controlled release matrix can be any of the matrix release systems known in the pharmaceutical arts. In general, such a matrix is based on water-insoluble polymeric materials as a matrix-forming carrier agent. Generally the preferred material is hydrophilic but water insoluble or slightly water soluble. Typically, the carrier material forms a non-disintegrating, non-dissolving, porous matrix. Various hydrophilic polymers can be used as matrix forming agents in the compositions of the present invention including appropriate hydroxypropyl methylcellulose(s) (HPMC), polyacrylates, polymethacrylates, etc. Additionally, the tablet core typically contains at least one binder/filler. A binder/filler is used to bind various components of a tablet. It is desirable to have an elastic binder/filler in the core tablet to compensate for the relaxation, if any, of the matrix-forming agent, particularly when an HPMC is used as the matrix material. Different types of binders/fillers can be used including microcrystalline cellulose(s) ("MCC"), PVP, starch, hydroxypropyl cellulose, etc.

In addition, the following excipients may be also present in the composition:

a) Hydrophilic filler: This is used to facilitate the solubility of the drug substance in the matrix, if necessary, and support the diffusion of drug substance via the matrix network. Various hydrophilic fillers can be used, lactose, mannitol, sorbitol (as a general any polyols), etc.

b) Buffering agent: In order to increase the solubility of zolpidem in the intestinal tract, where the pH is higher than in the stomach, it is advantageous to create an acidic microenvironment. For this reason, different types of organic or non-organic acids may be used. Typically tartaric acid is used.

c) Glidant: For better flow of powders during tabletting, it is useful to use appropriate glidant(s), for instance colloidal silicon dioxide.

d) Lubricant: To avoid adherence of powders to punches, it is common to use a suitable lubricant. Examples include magnesium stearate and sodium stearyl fumarate.

The inner tablet core is typically designed to allow release of the zolpidem such that 90% of the zolpidem is released in 1 to 6 hours. In contrast, the outer layer coat of the tablet is designed as an immediate release formulation wherein 90% of the zolpidem therein is released within 30 minutes.

The composition of the coating layer comprises zolpidem in an effective amount and at least one pharmaceutically acceptable excipient. An effective amount of zolpidem is generally at least 3 mg, usually at least 4 mg and more typically 5 to 10 mg. Greater amounts, including 20 mg, for example, can also be used but for sleep induction are generally not necessary. Typically, the coating composition contains at least one hydrophilic filler/binder. The main purpose is to bind the components of the coat in a non-friable and sufficiently hard layer. Advantageously, the component(s) are selected in such a way that it increases the elastic properties of the blend and allows for adhesion of the outer core to the inner core via compression. Different types of binders can be used including MCC especially PH 102, appropriate HPMC such as E5, PVP, Starch, hydroxypropyl cellulose, etc. Additionally, water soluble filler is conveniently used such as lactose, mannitol, sorbitol (as a general any polyols), etc. And the coating layer typically contains a disintegrant in order to obtain a burst release profile. Sodium starch glycollate is the preferred disintegrant compound, but crosspovidone, crosscarmelose sodium, etc., can also be used. The layer coat can also contain a glidant and/or lubricant as described above for the tablet core.

In addition to the above ingredients, either or both of the tablet core and coating layer may contain one or more wetting agents such as sodium lauryl sulfate, cetyl alcohol, docusate sodium, polyoxylene alkyl ethers etc., and/or plasticizing agents such as triethyl citrates, dibutyl phthalate, glycerol, triacetin, castor oil, polyethylene glycol, etc.

In order to form pharmaceutically acceptable and/or elegant tablets, the core:coating mass ratio and/or coating layer binder content should be taken into account. As the mass ratio becomes larger, the useful range of binder content in the coating layer becomes wider. As the mass ratio becomes smaller, a higher amount of binder is generally needed in the coating layer. Thus, at a core:coating mass ratio of 1:1.8, at least 34% of binder should be present in the coating layer. This amount of binder can be in a single kind of binder or the total of two or more binders, e.g. 30% MCC and 5% HPC represents 35% binder. Similarly, as the ratio becomes larger such as 1:2, then less binder can be used, such as 29% or more. As the ratio exceeds 1:2.5, the lower limit of binder becomes less important. For practical reasons, generally the coating layer contains at least 10% binder and not more than 80% binder. Typically the coating layer contains binder in the amount of 20-50%, subject to the above mass ratio limitations; i.e. at 1:1.8 mass ratio then the binder range would be typically 34-50%.

Generally the mass of the coating layer is at least 2.5 times greater than the mass of the tablet core and in some embodiments, the coating layer is at least 3 times, usually 3 to 5 times, and generally about 4 times greater than the mass of the tablet core.

In some embodiments of the present invention, at least 50%, and typically at least 60% of the tablet core is made up of an HPMC and MCC; and at least 60%, typically at least 80% of the coating layer is made up of an MCC and a polyol, especially lactose.

In other embodiments of the invention, the tablet core and coating layer have the following compositions:

Tablet Core
5 to 20% of zolpidem;
15 to 40% of an HPMC;
30 to 55% of an MCC;
0 to 20% of a polyol; and
2 to 20% of an acid.
Coating Layer
1 to 10% of zolpidem;
20 to 40% of an MCC;
40 to 80% of a polyol;
0 to 10% of an HPMC; and
1 to 10% of a disintegrant.

In a preferred form either or both of the tablet core and coating layer compositions contain 0 to 5% of one or more additional excipients, typically lubricant(s), glidant(s), etc.

The relative amount and/or size of the tablet core to the coating layer has also been found to have an effect on the quality and practicality of the final tablet. From a practical perspective the total mass of the core tablet is generally within the range of 30 to 100 mg, more typically 50 to 70 mg. The mass of the coating layer is generally within the range of 150 to 300 mg, more typically 220 to 260 mg. The core tablet as well as the coated tablet are normally the same shape, preferably round including flat round or more typically convex round tablet shape. The core tablet usually has a diameter of 7 millimeters or less, usually 6 millimeters or less. The coated tablet preferably has a diameter of about 11 millimeters or less, typically 9 to 10.5 millimeters and in some embodiments preferably about 10 millimeters.

The mass of the tablet core and the coating layer as well as the percentage therein of zolpidem can be adjusted to provide the desired amount of zolpidem in each phase. The tablet core, which serves to provide an extended duration, may suitably contain from 2 to 20 mg of zolpidem, typically 3 to 10 mg of zolpidem. The coating layer generally contains 3 to 20 mg, typically 4 to 10 mg of zolpidem. In some embodiments the tablet core and the coating layer contain the same amount of zolpidem. Overall the total amount of zolpidem is generally 40 mg or less such as within the range of 5 to 30 mg, more typically 6 to 15 mg, and in some embodiments 6.25 and 12.5 mg of zolpidem. For clarity, the amount of zolpidem as used throughout this application refers to the mass of zolpidem calculated (or expressed as) as the tartrate salt; i.e. the weight corresponds to the weight of a molar equivalent amount of zolpidem tartrate.

Preferably the coating layer of the tablet-in-tablet dosage form of the invention is formed by direct compression and more preferably the core tablet is also made by direct compression. That is, the above components for both the tablet core and the coating layer are so selected that they would allow for making the tablets by direct compression. The weighed amount of ingredients may then be blended together in a dry state, i.e. without a need of a granulation process, and subjected directly to the compression process. Thus, in a preferred method a powder blend made from the tablet core-forming ingredients is mixed with a small amount of lubricant and is compressed in a tablet punch to form a tablet; e.g. a round tablet of diameter 6 mm. This tablet forms the tablet core of the final "tablet-in-tablet". Then a second, larger tablet punch, e.g. round diameter 10 mm, is partially charged with a small amount of a powder blend made from the coating layer-forming ingredients. The previously produced tablet core is placed and centered in the partially charged punch, additional coating layer powder blend is added and the whole material compressed to form a compression coating layer around the tablet core; e.g. a tablet-in-tablet. Tablet presses allowing such a technique are known as alternate tablet presses or "tablet-in tablet" presses and are known in the art. While the coating layer is preferably formed directly on the tablet core, it is contemplated within the present invention that intervening layers may be present between the core tablet and the coating layer. Such intervening layers, if present, would generally be formed by coating the core tablet, such as by film coating, etc., prior to forming the compression coating layer.

In the tabletting process, it is frequently desirable that the time between making the core tablet and forming the coating layer thereon is at least several hours. This is because the matrix components of the core are frequently elastic (particularly when using cellulose and its derivatives as excipients) and they may expand after the compression of tablet formation. Therefore, it is advantageous to "equilibrate the volume" of the core tablet by allowing it to be contacted with a normal environment for some time; e.g. at least 3 hours such as 3 to 12 hours or longer, prior to being subjected to the coating. This will minimize the capping of the produced tablets.

The tablets of the invention may be finally coated by a thin film coating to prevent undesired action of the external environment during handling and storage and to enhance handling and cosmetic properties. It must however be pointed out that this film coating should be rapidly dissolvable in the stomach environment (a non-enteric coating) to minimize the latent period prior to release and should not have any other influence on the release characteristics. Typically any such coating serves only "cosmetic" purposes such as taste masking, surface improvement, etc. A suitable film-coating material is that as sold under commercial brand name Opadry. The amount of film coat typically does not exceed 3% of the total mass. Nonetheless, the tablets usually do not contain any kind of surface coating.

The tablets of the invention can exhibit physical parameters (hardness, friability) comparable with those of conventional tablets. The tablets of the present invention can be used in a method for inducing or maintaining sleep and/or in methods of treatment of sleep disorders. Such methods comprise administering an effective hypnotic amount of the tablets to the patient in need thereof. In preferred embodiments, the administration of a single tablet of the invention provides for a duration of action of about 6 to 8 hours. Similarly, the tablets of the present invention can be used in methods for treating Parkinson's disease, parkinsonian syndromes and other disorders treatable by zolpidem by administering an effective amount of the zolpidem within the tablet to a patient in need thereof.

The tablets may be administered in dosage amounts and regimens corresponding to those known and recommended in the art. The invention will be further illustrated by way of the following non-limiting examples.

EXAMPLES

Example 1

Formulation of the Tablet Core

|  | Core for the 12.5 mg strength | | Core for the 6.25 mg strength | |
| --- | --- | --- | --- | --- |
|  | (%) | (mg) | (%) | (mg) |
| Zolpidem tartrate | 10.42 | 6.25 | 5.208 | 3.125 |
| Hydroxypropyl Methyl cellulose K4M | 25 | 15 | 25 | 15 |
| Microcrystalline cellulose | 40.58 | 24.35 | 45.792 | 27.475 |
| Lactose monohydrate | 10 | 6 | 10 | 6 |
| Tartaric acid | 12 | 7.2 | 12 | 7.2 |
| Silica dioxide | 0.5 | 0.3 | 0.5 | 0.3 |
| Mg stearate | 1.5 | 0.9 | 1.5 | 0.9 |
| Tablet mass | 60 mg | | 60 mg | |
| Tablet diameter | 6 mm | | 6 mm | |

Formulation of the Outer Coat and the Final Tablet

|  | Coat for 12.5 mg strength | | Coat for 6.25 mg strength | |
| --- | --- | --- | --- | --- |
|  | (%) | (mg) | (%) | (mg) |
| Zolpidem tartrate | 2.6 | 6.25 | 1.3 | 3.125 |
| Hydroxypropylmethyl cellulose (HPMC) E5 | 5.0 | 12 | 5.0 | 12 |
| Microcrystalline cellulose (MCC) PH 102 | 25.0 | 60 | 25.0 | 60 |
| Lactose monohydrate | 63.2 | 151.68 | 64.5 | 154.795 |
| Sodium starch glycollate | 3.2 | 7.68 | 3.2 | 7.68 |
| Mg stearate | 1.0 | 2.4 | 1.0 | 2.4 |
| Total Tablet Mass | 300 mg | | 300 mg | |
| Tablet Diameter | 10 mm | | 10 mm | |

Manufacturing Process

Step 1—Tablet Core:

Silicon dioxide was sieved over a 0.6 mm sieve and tartaric acid was sieved over a 0.315 mm sieve. Zolpidem tartrate, hydroxypropylmethyl cellulose, microcrystalline cellulose, lactose and tartaric acid were mixed for 30 minutes in the free fall mixer at 25 rpm. Magnesium stearate was sieved over a 0.8 mm sieve and added to the blend. The blend was mixed for 5 minutes at 25 rpm. The tablets were compressed at the Korsch PH 106 tablet press, yielding a tablet of weight of 60 mg, a tablet diameter of 6 mm, and good tablet hardness.

Step 2—Tablet-in-Tablet:

Zolpidem was mixed with a part of the microcrystalline cellulose (ratio 1:6) in the Turbula free fall mixer at 22 rpm for 10 minutes. The preblend was mixed with hydroxypropylmethyl cellulose, remaining microcrystalline cellulose, lactose and sodium starch glycolate for 20 min in the free fall mixer at 25 rpm. The magnesium stearate was sieved through a 0.8 mm sieve and added to the blend. The blend was mixed for another 5 minutes at 25 rpm. The blend was tabletted together with the tablet core prepared in the step 1 in the Killian tablet-in-tablet apparatus.

The total tablet mass was 300 mg, the tablet diameter was 10 mm, and the hardness was good. The total tablet consists of 60 mg modified release inner tablet core and 240 mg immediate release outer coating layer, wherein half of the total zolpidem was contained in each of the tablet core and coating layer.

Example 2

Using the formulations as described below, tablets were made as follows. Silicon dioxide was sieved over 0.6 mm sieve and tartaric acid was sieved over 0.315 mm sieve. Zolpidem tartrate, HPMC, MCC, lactose, and silicon dioxide were mixed for 30 minutes at 25 prm. Magnesium stearate was sieved over 0.8 mm sieve, added to the blend, and mixed for another 5 minutes at 22 rpm. Tablets were made on the Korsch PH 106. The tablets had a diameter of 8 mm, mass of 120 mg, and hardness of 30 N.

The blend for the coating layer (shell) was made as follows. Zolpidem tartrate and MCC in a 1:6 ratio were mixed for 10 minutes in a Turbula at 22 rpm. The remaining excipients, except magnesium stearate were added and the blend was mixed for another 20 minutes in a Turbula free fall mixer at 22 rpm. The magnesium stearate was sieved through a 0.8 mm sieve, added to the blend, and mixed for another 5 minutes at 22 rpm. The blend was used to compress a coating on the tablets using a Killian tablet-in-tablet machine.

The tablet formulations are based on the following standard formulation:

| Core | |
| --- | --- |
| Zolpidem tartrate | 5.21% |
| Lactose | 10% |
| MCC | 45.79% |
| HPMC | 25% |
| Tartaric acid | 12% |
| Silicon dioxide | 0.5% |
| Magnesium Stearate | 1.5% |
| Tablet mass | 120 mg |
| Tablet diameter | 8 mm |
| Compression coating | |
| Zolpidem tartrate | 2.604% |
| HPMC E5 | 5% |
| MCC | 25% |
| Lactose | 63.196% |
| Sodium starch glycolate | 3.2% |
| Magnesium Stearate | 1.5% |
| Tablet mass | 240 mg |
| Tablet diameter | 11 mm |

Tablet-in-tablets were made based on the standard tablet formulation above, but having different masses, diameters, hardnesses, and/or coating layer binder amounts from the standard tablet. The compression coating was varied in total weight and percentage MCC. The variation in percentage MCC was corrected by lactose. The variation in percentage zolpidem in the formulation due to mass variation was corrected by lactose as well. The results are shown in the following Table.

| Experiment | Coating Binder* | Punch diameter | Mass Ratio core:coating theoretical | Compression Force (kN) | Hardness (N) | Capping on Friability |
|---|---|---|---|---|---|---|
| 1 | 25% MCC | 10 | 1:2.5 | 4 | 64 | N |
| 2 | 25% MCC | 10 | 1:2.5 | 10 | 93 | N |
| 3 | 25% MCC | 11 | 1:2.5 | 4 | 56 | N |
| 4 | 25% MCC | 11 | 1:2.5 | 10 | 78 | N |
| 5 | 25% MCC | 11 | 1:2.5 | 18 | 69 | N |
| 6 | 25% MCC | 12 | 1:2.5 | 4 | 30 | Y |
| 7 | 25% MCC | 12 | 1:2.5 | 8 | 45 | N |
| 8 | 0% HPC 25% MCC | 11 | 1:2.5 | 4 | 49 | N |
| 9 | 0% HPC 25% MCC | 11 | 1:2.5 | 10 | 45 | N |
| 10 | 0% HPC 25% MCC | 11 | 1:2.5 | 14 | 56 | N |
| 11 | 25% MCC | 11 | 1:2.25 | 4 | 49 | N |
| 12 | 25% MCC | 11 | 1:2.25 | 10 | 50 | N |
| 13 | 25% MCC | 11 | 1:2.25 | 14 | 70 | N |
| 14 | 25% MCC | 11 | 1:2 | 4 | 22 | Y |
| 15 | 25% MCC | 11 | 1:2 | 10 | 30 | Y |
| 16 | 25% MCC | 11 | 1:2 | 13 | 49 | N |
| 17 | 25% MCC | 11 | 1:1.8 | 4 | 22 | Y |
| 18 | 25% MCC | 11 | 1:1.8 | 10 | 19 | Y |
| 19 | 75% MCC | 11 | 1:1.8 | 4 | 80 | N |
| 20 | 75% MCC | 11 | 1:1.8 | 8 | 102 | N |
| 21 | 50% MCC | 11 | 1:1.8 | 4 | 60 | N |
| 22 | 50% MCC | 11 | 1:1.8 | 10 | 72 | N |
| 23 | 50% MCC | 11 | 1:1.8 | 14 | 77 | N |
| 24 | 33% MCC | 11 | 1:1.8 | 4 | 45 | N |
| 25 | 33% MCC | 11 | 1:1.8 | 10 | 61 | N |
| 26 | 33% MCC | 11 | 1:1.8 | 14 | 61 | N |
| 27 | 29% MCC | 11 | 1:1.8 | 4 | 44 | N |
| 28 | 29% MCC | 11 | 1:1.8 | 10 | 59 | N |
| 29 | 29% MCC | 11 | 1:1.8 | 18 | 62 | N |

*The coating layer binder also includes 5% HPC as in the standard formulation unless otherwise indicated.

Each of the patents mentioned above is incorporated herein by reference. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A zolpidem oral tablet, comprising:
   (a) an inner tablet core comprising zolpidem or a pharmaceutically acceptable salt thereof and a controlled release matrix, wherein said tablet core comprises 5 to 20% of said zolpidem or pharmaceutically acceptable salt, 15 to 40% of an HPMC, 30 to 55% of an MCC, 0 to 20% of a polyol, 2 to 20% of an acid, and 0 to 5% of one or more additional excipients; and
   (b) a compressed coating layer surrounding said inner tablet core, which comprises an effective amount of zolpidem or a pharmaceutically acceptable salt thereof and at least one pharmaceutically acceptable excipient, wherein said coating layer comprises 1 to 10% of said zolpidem or a pharmaceutically acceptable salt thereof, 20 to 40% of an MCC, 40 to 80% of a polyol, 0 to 10% of an HPMC, 1 to 10% of a disintegrant, and 0 to 5% of one or more additional excipients;
   wherein
   the mass of said coating layer is at least 2.5 times the mass of said tablet core.

2. The zolpidem tablet according to claim 1, wherein said tablet core has a mass within the range of 30 to 100 mg.

3. The zolpidem tablet according to claim 2, wherein said coating layer has a mass within the range of 150 to 300 mg.

4. The zolpidem tablet according to claim 1, wherein said tablet has a diameter within the range of 9 to 10.5 millimeters.

5. The zolpidem tablet according to claim 4, wherein said coating layer is about four times the mass of said tablet core.

6. The zolpidem tablet according to claim 1, wherein the total amount of zolpidem or its pharmaceutically acceptable salt contained in the tablet is within the range of 5 to 30 mg.

7. The zolpidem tablet according to claim 6, wherein said tablet core contains 2 to 20 mg of zolpidem or a pharmaceutically acceptable salt thereof and said coating layer contains 3 to 20 mg of zolpidem or a pharmaceutically acceptable salt thereof, each expressed in terms of zolpidem tartrate.

8. The zolpidem tablet according to claim 6, wherein the zolpidem is zolpidem tartrate.

9. The zolpidem tablet according to claim 8, wherein the total amount of zolpidem tartrate contained in the tablet is 6.25 mg or 12.5 mg.

10. The zolpidem tablet according to claim 6, wherein the amount of zolpidem in the tablet core is identical to the amount of zolpidem in the coating layer.

11. The zolpidem tablet according to claim 1, wherein said tablet is a direct compression tablet.

12. The zolpidem tablet according to claim 1, which further comprises a film coating surrounding said tablet.

13. The zolpidem tablet according to claim 1, wherein said tablet has a diameter of about 11 millimeters or less.

14. The zolpidem tablet according to claim 13, wherein said tablet core has a mass within the range of 50-70 mg and has a diameter of about 7 millimeters or less; and said coating layer has a mass within the range of 220 to 260 mg.

* * * * *